(12) United States Patent
Honge

(10) Patent No.: US 11,512,722 B2
(45) Date of Patent: Nov. 29, 2022

(54) DEVICE REPLACEMENT IN WEARABLE ARTICLE MANUFACTURING EQUIPMENT

(71) Applicant: ZUIKO CORPORATION, Osaka (JP)

(72) Inventor: Susumu Honge, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 17/750,312

(22) Filed: May 21, 2022

(65) Prior Publication Data

US 2022/0275815 A1 Sep. 1, 2022

Related U.S. Application Data

(62) Division of application No. 16/759,131, filed as application No. PCT/JP2018/040968 on Nov. 5, 2018, now Pat. No. 11,365,752.

(30) Foreign Application Priority Data

Nov. 14, 2017 (JP) ................................ 2017-218960

(51) Int. Cl.
| | |
|---|---|
| *A61F 13/15* | (2006.01) |
| *F16M 1/00* | (2006.01) |
| *F16B 5/00* | (2006.01) |
| *F16B 5/02* | (2006.01) |

(52) U.S. Cl.
CPC ........ *F16B 5/008* (2013.01); *A61F 13/15804* (2013.01); *F16B 5/02* (2013.01); *F16M 1/00* (2013.01)

(58) Field of Classification Search
CPC ....... F16B 5/008; F16B 5/02; A61F 13/15804
See application file for complete search history.

(56) References Cited

U.S. PATENT DOCUMENTS 6,273,165 B1 * 8/2001 Gundersen ........ A61F 13/15804
156/367
8,321,049 B2 11/2012 Healey et al.

FOREIGN PATENT DOCUMENTS

| JP | H04-96891 U | 8/1992 |
| JP | H06-2750 U | 1/1994 |
| JP | H06-13774 A | 1/1994 |

(Continued)

OTHER PUBLICATIONS

International Search Report Issued in PCT/JP2018/040968 dated Jan. 29, 2019.

*Primary Examiner* — Jason L Vaughan
*Assistant Examiner* — Amanda Kreiling
(74) *Attorney, Agent, or Firm* — Renner, Otto, Boisselle & Sklar, LLP

(57) ABSTRACT

A panel attachment structure for a wearable article manufacturing equipment includes: lower and upper panels vertically arranged while separated up-and-down; a first processing section and a first driving section respectively attached to a front face and a back face of the lower panel; a second processing section and a second driving section respectively attached to a front face and a back face of the upper panel; a base horizontally arranged under the lower panel; and a pair of pillars raised from the base, wherein, in the structure, the lower and upper panels are removably fixed to the pillars while being supported by the respective lower and upper parts of the pillars, and each pillar has a support section, provided between the upper and lower panels and supporting the load of the upper panel.

3 Claims, 10 Drawing Sheets

(56) References Cited

FOREIGN PATENT DOCUMENTS

| | | | |
|---|---|---|---|
| JP | H09-232776 | A | 9/1997 |
| JP | H10-505246 | A | 5/1998 |
| JP | 2005-200117 | A | 7/2005 |
| JP | 2007-044349 | A | 2/2007 |
| WO | 01-56523 | A1 | 8/2001 |

* cited by examiner

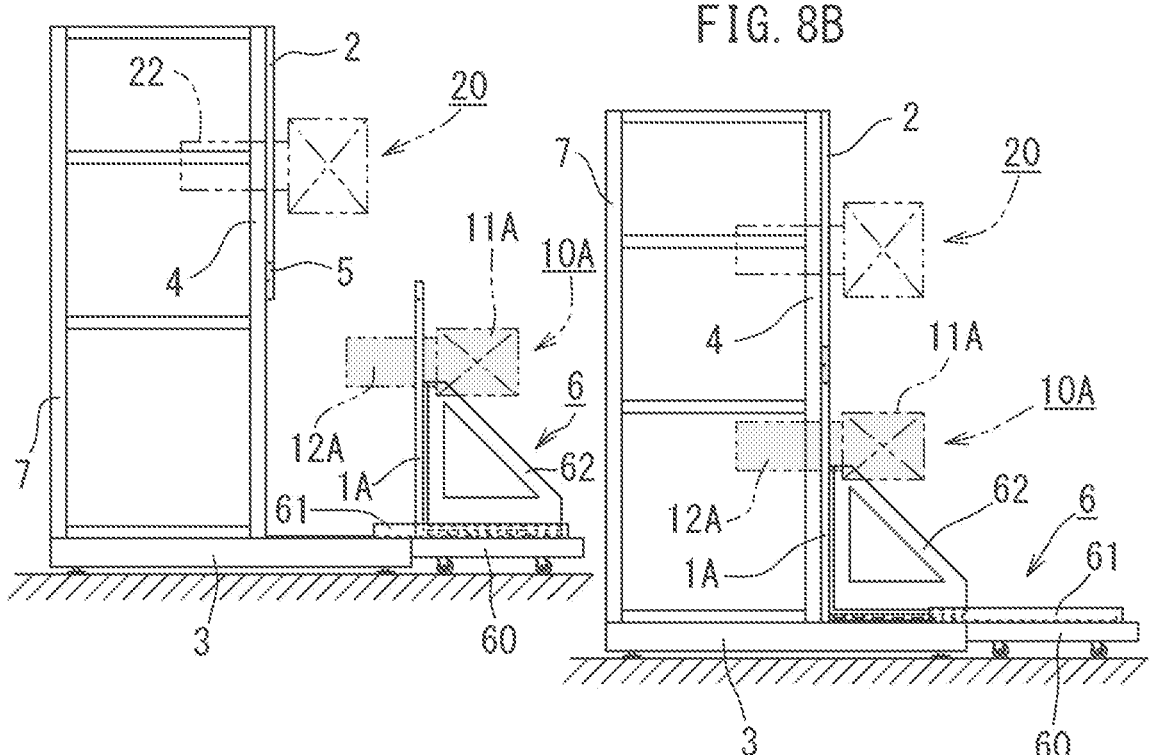
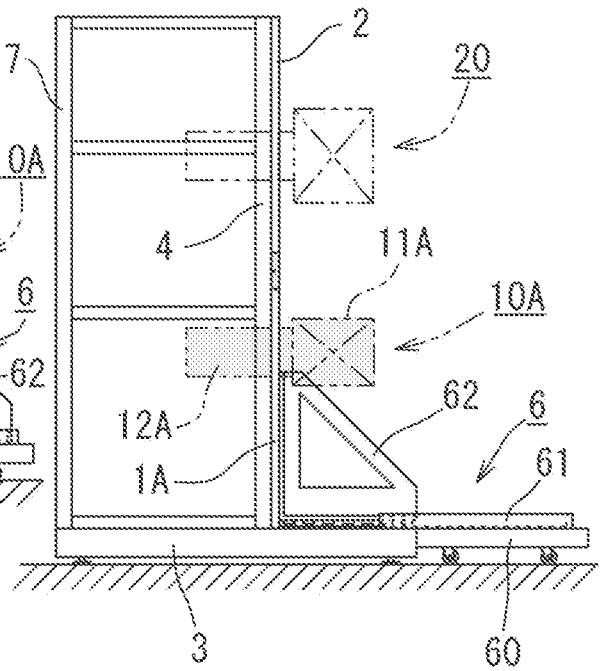
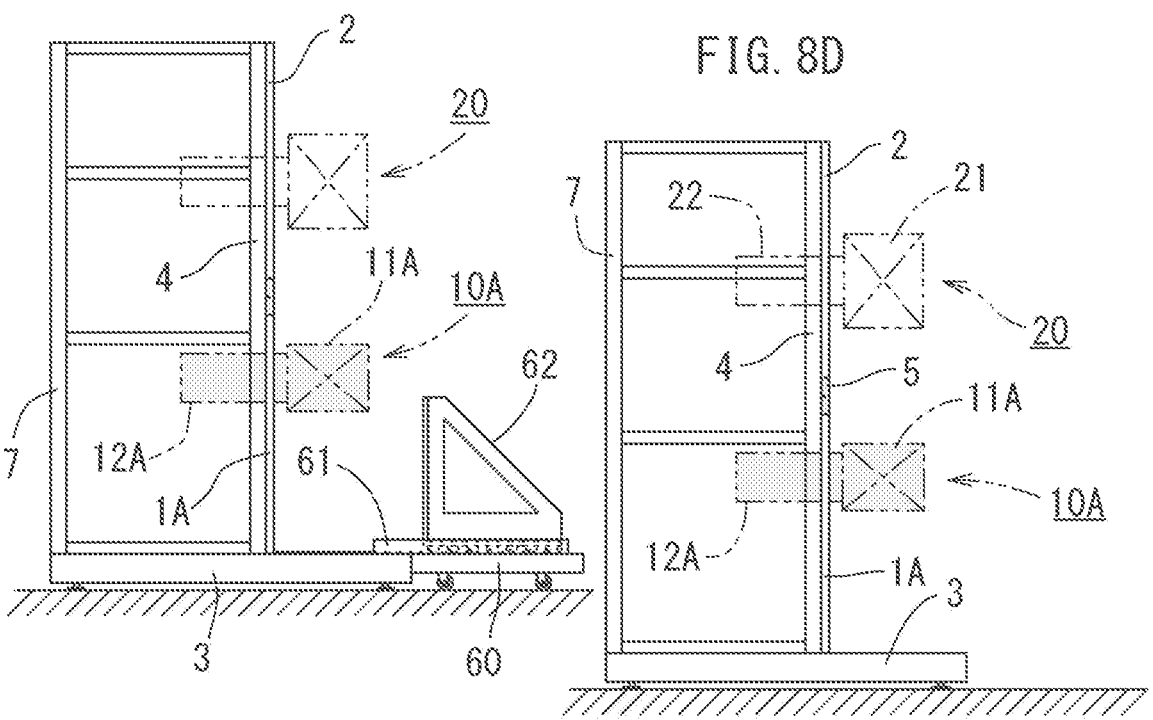
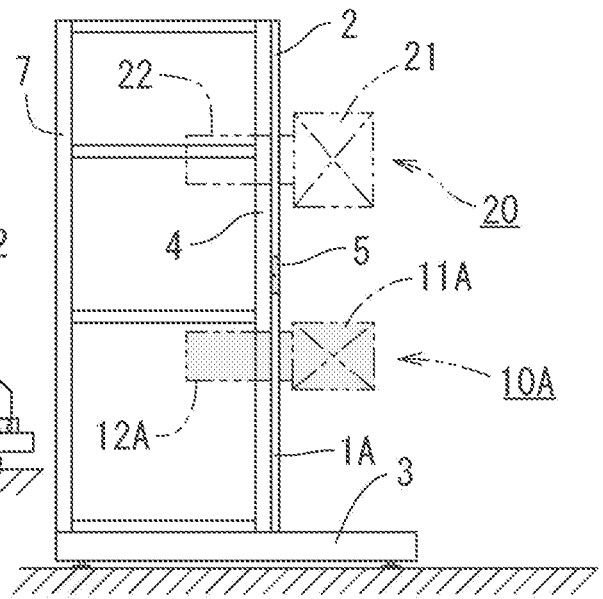

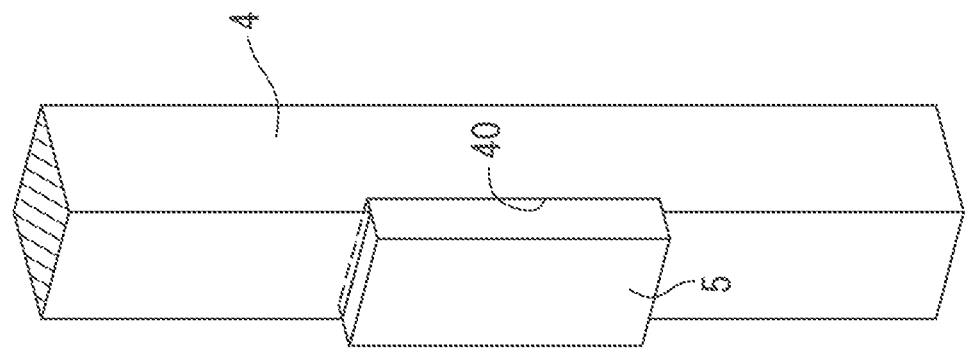
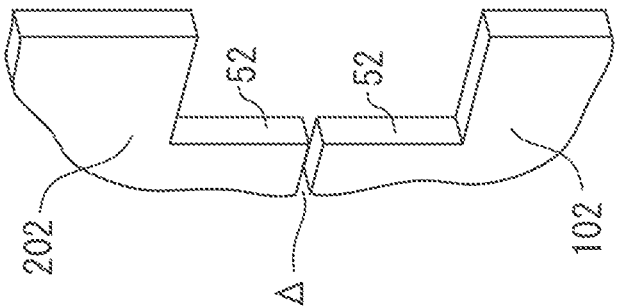
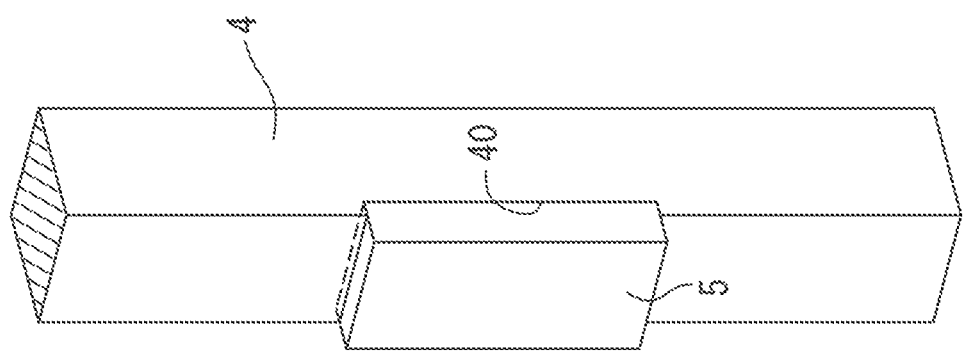
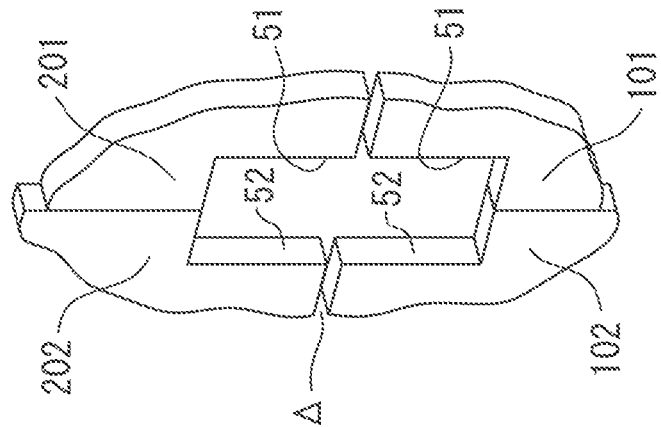
FIG. 9

DEVICE REPLACEMENT IN WEARABLE ARTICLE MANUFACTURING EQUIPMENT

This is a divisional application under 35 USC § 121 of U.S. application Ser. No. 16/759,131, filed on Apr. 24, 2020, which is a National Stage under 35 USC § 371 of International Application No. PCT/JP2018/040968, filed on Nov. 5, 2018, which claims priority under 35 USC § 119 to Japanese Application No. 2017-218960, filed Nov. 14, 2017, the entire disclosures of which are incorporated herein in their entirety.

Technical Field

The present invention relates to replacement of devices in a wearable article manufacturing equipment.

Background Art

In recent years, frames for supporting devices have been modularized in wearable article manufacturing equipment. The modularized frame is arranged in a plural number or in a great number, as disclosed in the following patent documents. The devices supported by the respective frames produce wearable articles in a continuous manner. Each module includes a base, a pair of pillars, and one set of upper and lower panels (see the patent documents 1 and 2 listed below). The disclosure of the following patent documents is herein entirely incorporated.

The respective upper and lower panels are tightened to a pair of pillars by bolts, for example. Each panel is configured as one unit so that a processing section and a driving section are attached to a front face and a back face, respectively. In order to change the size for example, each unit is removed from the pillars together with the respective panels and is replaced.

PRIOR ART LITERATURE

Patent Literature

[The First Patent Document] PCT/US2001/003188 (FIG. 1 to FIG. 8)
[The Second Patent Document] JP2005-200177 (Front page)

SUMMARY OF INVENTION

However, in the case of the invention of the above document 1, the load of an upper panel is supported by a lower panel. Thus, in order to replace the first processing section and/or the driving section attached to the lower panel, a step was required, prior to the removal of the lower panels from a pair of pillars, to remove the upper panel from the pair of pillars, thus requiring a long time to replace the unit.

It is an objective of the present invention to replace a device of a wearable article manufacturing equipment in a simple manner.

In one aspect, the present invention provides a panel attachment structure for a wearable article manufacturing equipment, the equipment including:
one set of a lower panel 1 and an upper panel 2 that are arranged along a vertical plane and that are provided while being separated in an up-and-down direction;
a first processing section 11 attached to a front face 1*f* of the lower panel 1;
a first driving section 12 attached to a back face 1*b* of the lower panel 1;
a base 3 that is provided under the lower panel 1 and that is arranged along a horizontal plane; and
a pair of pillars 4 raised from the base 3,
wherein, in the panel attachment structure, the lower panel 1 is removably fixed to the pair of pillars 4 in the state of being laid between lower parts of the pair of pillars 4,
the upper panel 2 is removably fixed to the pair of pillars 4 in the state of being laid between upper parts of the pair of pillars 4, and
support sections 5 are provided on respective pillars of the pair of pillars 4, the support sections 5 being arranged between the upper panel 2 and the lower panel 1, and supporting the load of the upper panel 2.

In this panel attachment structure, a first unit 10 including the lower panel 1, the first processing section 11, and the first driving section 12 is replaced in a manner as described below.

Specifically, this replacement method includes:
a step of removing the lower panel 1 from the pair of pillars 4 so as to remove the first unit 10 from the pair of pillars 4; and
a step of replacing the first unit 10 with a substitute first unit 10A by attaching the substitute first unit 10A to the pair of pillars 4, the substitute first unit 10A being as a substitute for the first unit 10 that has been removed from the pair of pillars 4,
wherein the removing step and the replacing step are performed in the state where the upper panel 2 is fixed to the pair of pillars 4.

As described above, the first processing section 11 and/or the first driving section 12 of the lower panel 1 can be replaced while the upper panel 2 is supported by the support section 5 in the state of being fixed to the pair of pillars 4. Thus, devices of a wearable article manufacturing equipment can be replaced in a simple manner.

BRIEF DESCRIPTION OF EMBODIMENTS

In FIG. 1 to FIG. 4, a processing section and a driving section attached to the upper and lower panels as well as penetration holes formed in the panels are omitted for the convenience of drawing figures. In order to better understand drawings, a support section in each figure is shown in gray.

Figure 5:
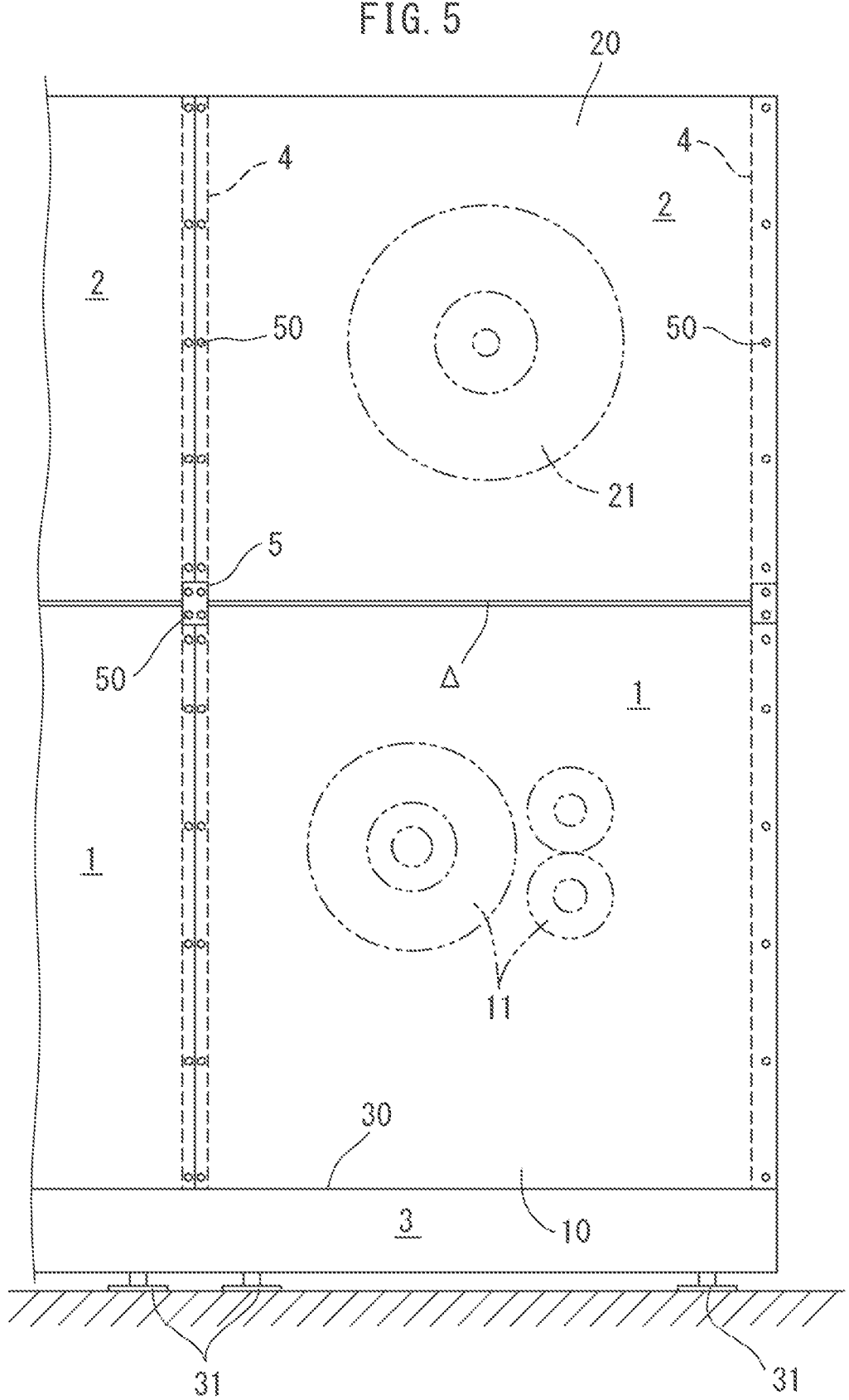

FIG. 5 is a schematic front view illustrating the panel attachment structure.

Figure 6:
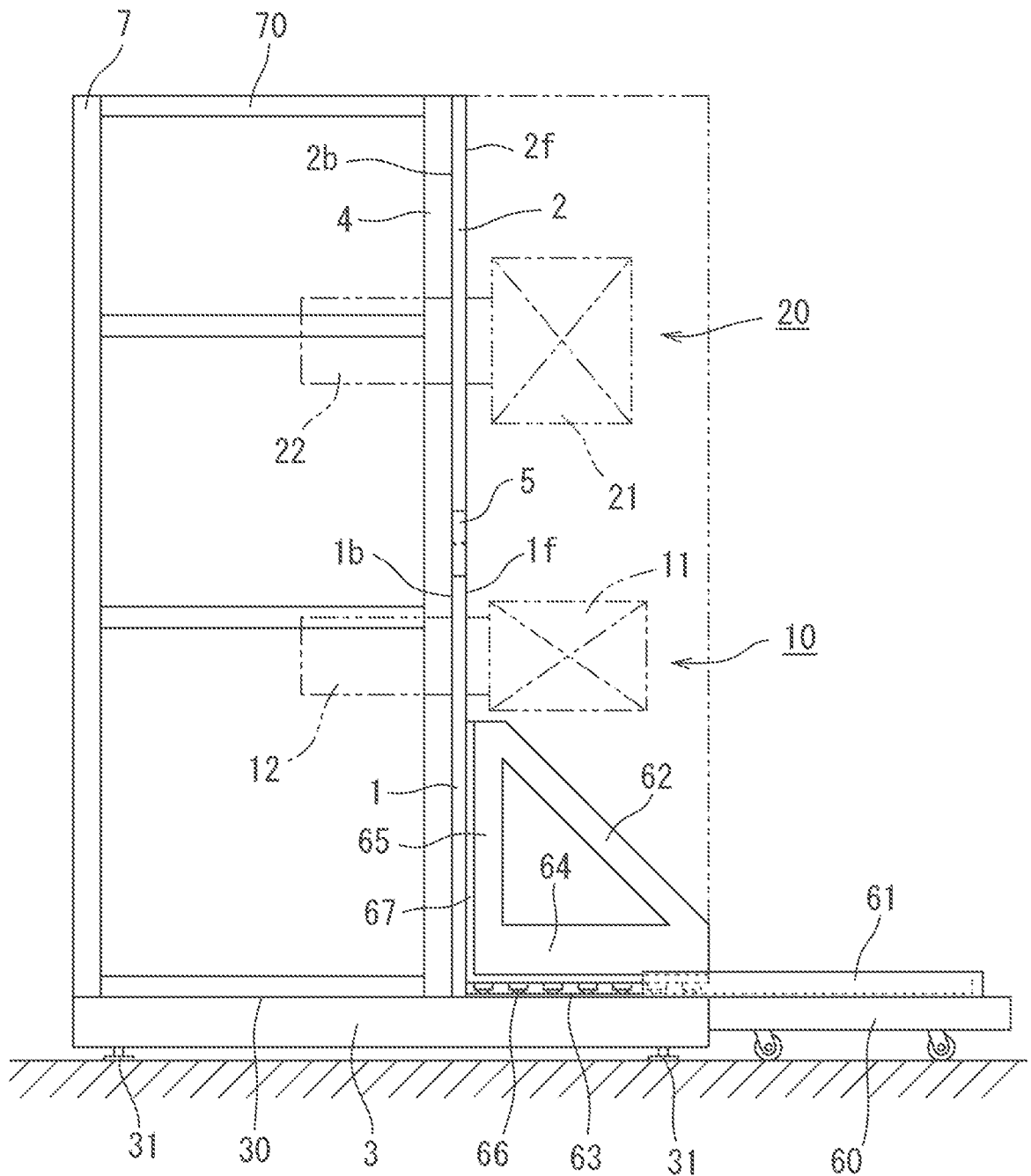

FIG. 6 is a schematic side view illustrating the attachment structure together with a replacement apparatus.

FIG. 7A to FIG. 7D are schematic side views illustrating a method of removing the first unit and the lower panel from the pillars in a sequential manner.

FIG. 8A to FIG. 8D are schematic side views illustrating a method of attaching the substitute first unit as a substitute together with the substitute lower panel as a substitute to the pillar in a sequential manner.

FIG. 9 is an exploded perspective view illustrating the relationship between the support section, the pillar, and the panels.

Figure 10A:
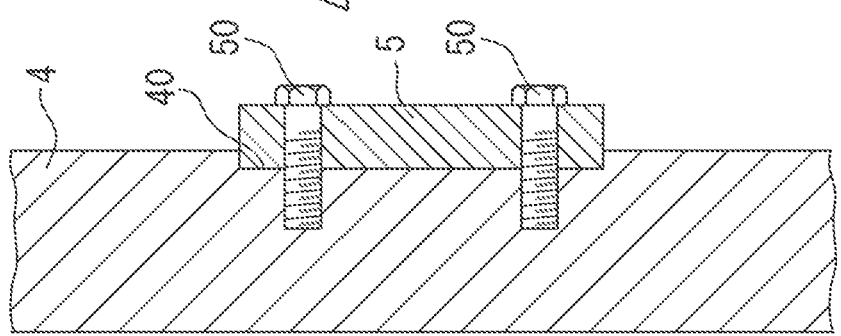
Figure 10B:
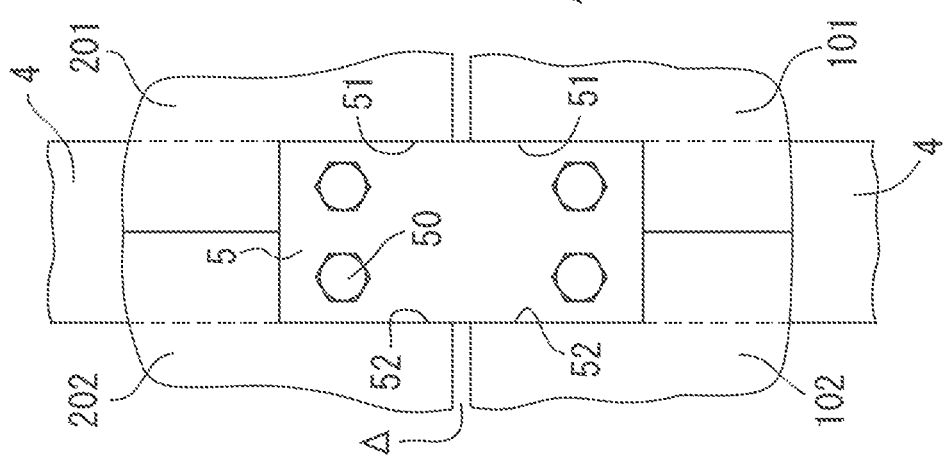
Figure 10C:
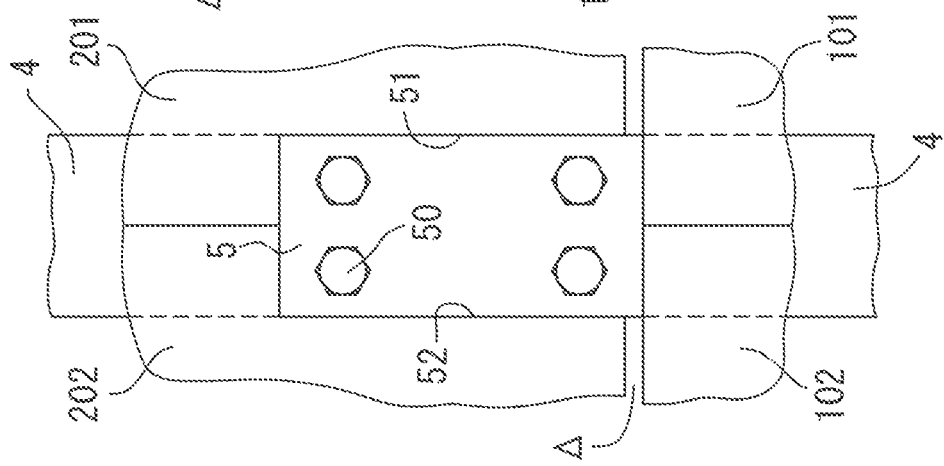
Figure 10D:
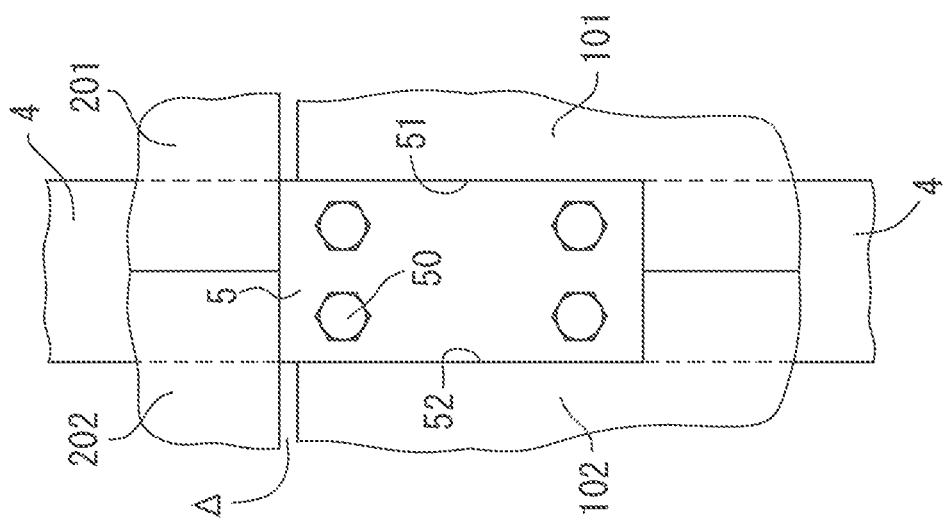

FIG. 10A is a cross-sectional view of the aforementioned relationship,

FIG. 10B is a front view of the aforementioned relationship, and FIG. 10C and FIG. 10D are front views illustrating respective different examples of the aforementioned relationship.

In FIG. 5 to FIG. 8D, in order to better understand drawings, the processing section and the driving section attached to the upper and lower panels are shown by two-dot chain lines. Penetration holes formed in the panels are omitted. The support sections are shown in gray. In order to better understand drawings, the substitute first driving section and the substitute first processing section in FIG. 8A to FIG. 8D are shown in gray. In FIG. 9, bolts are omitted.

DESCRIPTION OF EMBODIMENTS

Preferably, the support sections 5 are spacers 5 each fixed to an intermediate part of each of the pair of pillars, the intermediate part positioned between each of the upper parts and each of the lower parts; and the spacers 5 provide a space Δ between the lower panel 1 and the upper panel 2 by contacting with respective parts of a lower end of the upper panel 2.

In this case, the spacer 5 provides the space Δ between the lower panel 1 and the upper panel 2, thus allowing the lower panel 1 to be easily pulled from the pillars 4 to the front side.

Preferably, the support sections 5 are spacers 5 each fixed to each of the pair of pillars 4; and an upper end of each of the spacers 5 contacts with a corresponding lower-end corner of the upper panel 2, defining a space Δ between the lower panel 1 and the upper panel 2.

In this case, each corner of the lower end of the upper panel 2 is abutted to the upper end of each spacer, thus easily providing the space Δ.

Preferably, the upper panel 2 includes a lower-end first corner 201;
the lower panel 1 includes an upper-end first corner 101 facing the lower-end first corner 201;
a first notch 51 is formed in at least one of the lower-end first corner 201 and the upper-end first corner 101;
one of the spacers 5 is engaged with the first notch 51;
the upper panel 2 includes a lower-end second corner 202;
the lower panel 1 includes an upper-end second corner 102 facing the lower-end second corner 202;
a second notch 52 is formed in at least one of the lower-end second corner 202 and the upper-end second corner 102; and
another one of the spacers 5 is engaged with the second notch 52.

In this case, the spacers engaged with the respective notches allow the panels to be easily positioned, and provide the space Δ in an even easier manner.

In another aspect, the present invention provides a replacement unit 6 for replacing the first processing section 11 or the first driving section 12 according to claim 1, the replacement unit 6 including:

a carriage 60 movable relative to the base 3;

a pair of guides 61 that extends toward the lower panel 1 in a horizontal direction in the state where the carriage 60 is close to the base 3 functioning as a platform; and a slider 62 that is able to slide over the carriage 60 and the base 3 along the pair of guides 61, the slider 62 being able to be coupled with the lower panel 1, and the slider 62 being movable from the base 3 to the carriage 60 after coupled with the lower panel 1.

The method of the present invention uses the replacement unit 6 to replace the lower panel 1, the first processing section 11, and the first driving section 12. The method includes:

a step of moving the carriage 60 close to the base 3 that functions as the platform;

a coupling step of coupling the slider 62 with the lower panel 1, a step of removing, subsequent to the coupling step, the lower panel 1 from the pair of pillars 4 in order to remove the first unit 10 from the pair of pillars 4;

a step of transferring the first unit 10 and the slider 62 onto the carriage 60 along the guide 61; and a step of replacing the first unit 10 with a substitute first unit 10A by attaching the substitute first unit 10A to the pair of pillars 4, the substitute first unit 10A being as a substitute for the first unit 10 that has been removed from the pair of pillars 4, wherein the moving step, the coupling step, the removing step, the transferring step, and the replacing step are performed in the state where the upper panel 2 is fixed to the pair of pillars 4.

Even in this case, while the upper panel 2 is fixed to the pair of pillars 4, the first processing section 11 and/or the first driving section 12 of the lower panel 1 can be replaced. Thus, a device of a wearable article manufacturing equipment can be replaced in a simple manner.

In particular, the use of this replacement unit allows, even when the second unit 20 including the upper panel 2 is attached to the pillar 4, the first unit 10 to be pulled to the front side, thereby replacing the first unit 10 with the substitute first unit 10A as a substitute.

In this method, the wording "the base functioning as a platform" intends to express a situation where the carriage is stopped while close to the base and means that the base functions as a platform for the carriage.

Preferably, as the substitute first unit 10A,
the substitute first unit 10A is prepared prior to all the steps;
the substitute first unit 10A includes a substitute lower panel 1A as a substitute for the lower panel 1; and
the substitute lower panel 1A is attached with
i) a substitute first driving section 12A as a substitute for the first driving section 12, and
ii) a substitute first processing section 11A as a substitute for the first processing section 11.

In the present invention, the device that needs to be replaced is mainly the first processing section. When only a first processing section—a part of a first unit—is attempted to be replaced without replacing a lower panel and a first driving section, it requires a high skill and a lot of time to replace the first processing section due to the following steps: the lower panel is removed from pillars; the first processing section is removed from the removed lower panel; and a substitute first processing section, as a substitute for the removed first processing section, is attached to the removed lower panel at a wearable article production plant.

Thus, it is generally preferred to entirely replace the entire first unit integrated to include not only the first processing section but also the first driving section and the lower panel. In this way, replacing the first unit with a substitute first unit becomes even easier.

However, in order to reduce the cost of a device, it is acceptable to replace only the first processing section.

Any feature illustrated and/or depicted in conjunction with one of the aforementioned embodiment(s) or the following example(s) may be used in the same or similar form in one or more of the other embodiments or other examples, and/or may be used in combination with, or in place of, any feature of the other embodiments or examples.

EXAMPLE

The present invention will be understood more clearly from the following description of preferred examples taken in conjunction with the accompanying drawings. Note however that the examples and the drawings are merely illustrative and should not be taken to define the scope of the present invention. The scope of the present invention shall be defined only by the appended claims. In the accompanying drawings, like reference numerals denote like components throughout the plurality of figures.

The following section will describe one example of the present invention based on the drawings.

Figure 1:
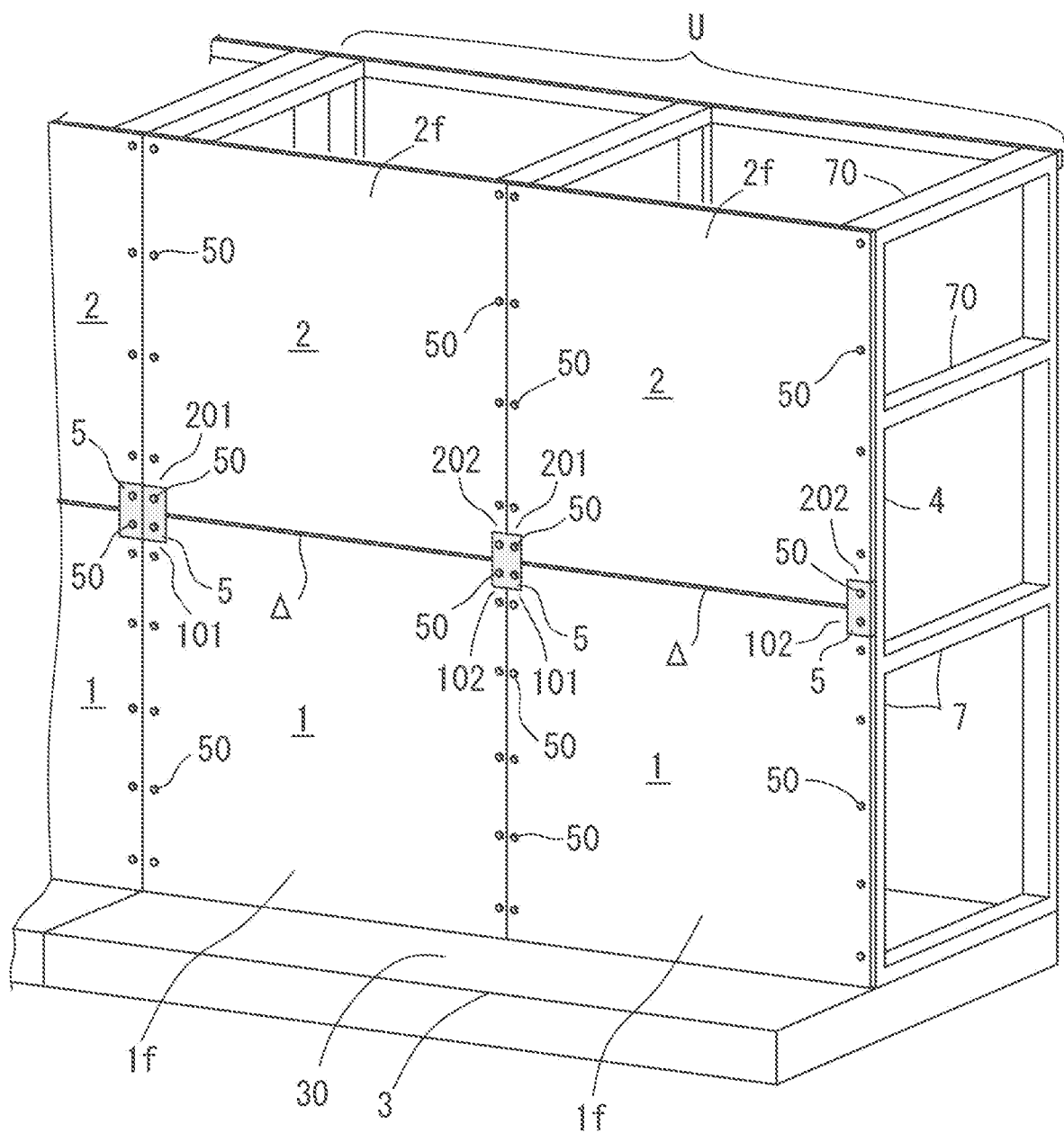
FIG. 1 is a schematic perspective view illustrating one example of a panel attachment structure of the present invention.

In FIG. 1, this manufacturing equipment may be configured so that a plurality or a great number of frame units U are connected with one another. The following section will describe the structure of one frame unit U prior to the description of the entire manufacturing equipment.

FIG. 1 and FIG. 6 illustrate one example of the frame unit U.

As shown in FIG. 1, the frame unit U includes the upper and lower panels 2 and 1, the base 3, and a frame-like frame 7. Note that the upper and lower panels 2 and 1 have a substantially rectangular plate-like shape.

The base 3 of FIG. 1 is formed to have a rectangular parallelepiped-like shape and is provided along a horizontal plane at the lower side of the lower panel 1. This base 3 is formed to have a box-like shape obtained by mutually welding a plurality of steel plates, for example. Note that the base 3 may have a plurality of leg sections 31 as shown in FIG. 6.

In FIG. 1, the frame-like frame 7 includes: a plurality of pillars 4 that is supported by a floor face and that is raised from the base 3 to extend in the perpendicular direction; and a beam 70 connecting the pillars 4. The frame 7 is formed to have a square frame-like (cubic lattice-like) shape. The frame-like frame 7 has one set of pillars 4 adjacent to each other between which a lower panel 1 and an upper panel 2 are fixed.

The upper panel 2 and a lower panel 1 are provided along the vertical plane and are arranged to be mutually separated so that the upper panel 2 is positioned directly above the lower panel 1. The lower panel 1 is fixed to one lower part of one of the pillars 4 and another lower part of another one of the pillars 4 in a removable manner by a plurality of bolts 50. The upper panel 2 is fixed to one upper part of one of the pillars 4 and another upper part of another one of the pillars 4 in a removable manner by a plurality of other bolts 50.

Each of the upper and lower panels 1 and 2 is configured so that one side edge of one panel is fixed along one pillar 4 and the other side edge is fixed along another pillar 4 separated from the one pillar 4 in the horizontal direction.

The support section 5 functioning as a spacer is fixed to the intermediate part between the upper part and the lower part of the pillar 4 by a plurality of still other bolts 50. This spacer 5 is intended to be abutted to a part of the lower end of the upper panel 2 to secure the space Δ between the lower panel 1 and the upper panel 2. Specifically, the spacer 5 is provided between the upper panel 2 and the lower panel 1 so as to support the load of the upper panel 2.

For example, as shown in FIG. 9, FIG. 10A, and FIG. 10B, the spacer 5 is fixed to each pillar 4 of the pair of pillars 4. The upper end of the spacer 5 is abutted to the corner of the lower end of the upper panel 2 to define the space Δ between the lower panel 1 and the upper panel 2.

As shown in FIG. 9 and FIG. 10A, each pillar 4 has a concave section 40 so that the concave section 40 may be engaged with the spacer 5.

Note that the panels 1 and 2 having a substantially-rectangular shape include notches corresponding to the spacer 5. Specifically, the upper panel 2 includes notches at both corners of its lower edge. On the other hand, the lower panel 1 includes notches at both corners of its upper edge.

For example, as shown in FIG. 10B, FIG. 10C, or FIG. 10D, the first notch 51 is formed in at least one of a first lower-end corner 201 of the upper panel 2 and a first upper-end corner 101 of the lower panel 1. The first upper-end corner 101 is opposed to the first lower-end corner 201. One of the spacers 5 is engaged with the first notch 51.

On the other hand, the second notch 52 is formed in at least one of a second lower-end corner 202 of the upper panel 2 and a second upper-end corner 102 of the lower panel 1. The second upper-end corner 102 is opposed to the second lower-end corner 201. Another one of the spacers 5 is engaged with the second notch 52.

Figure 4:
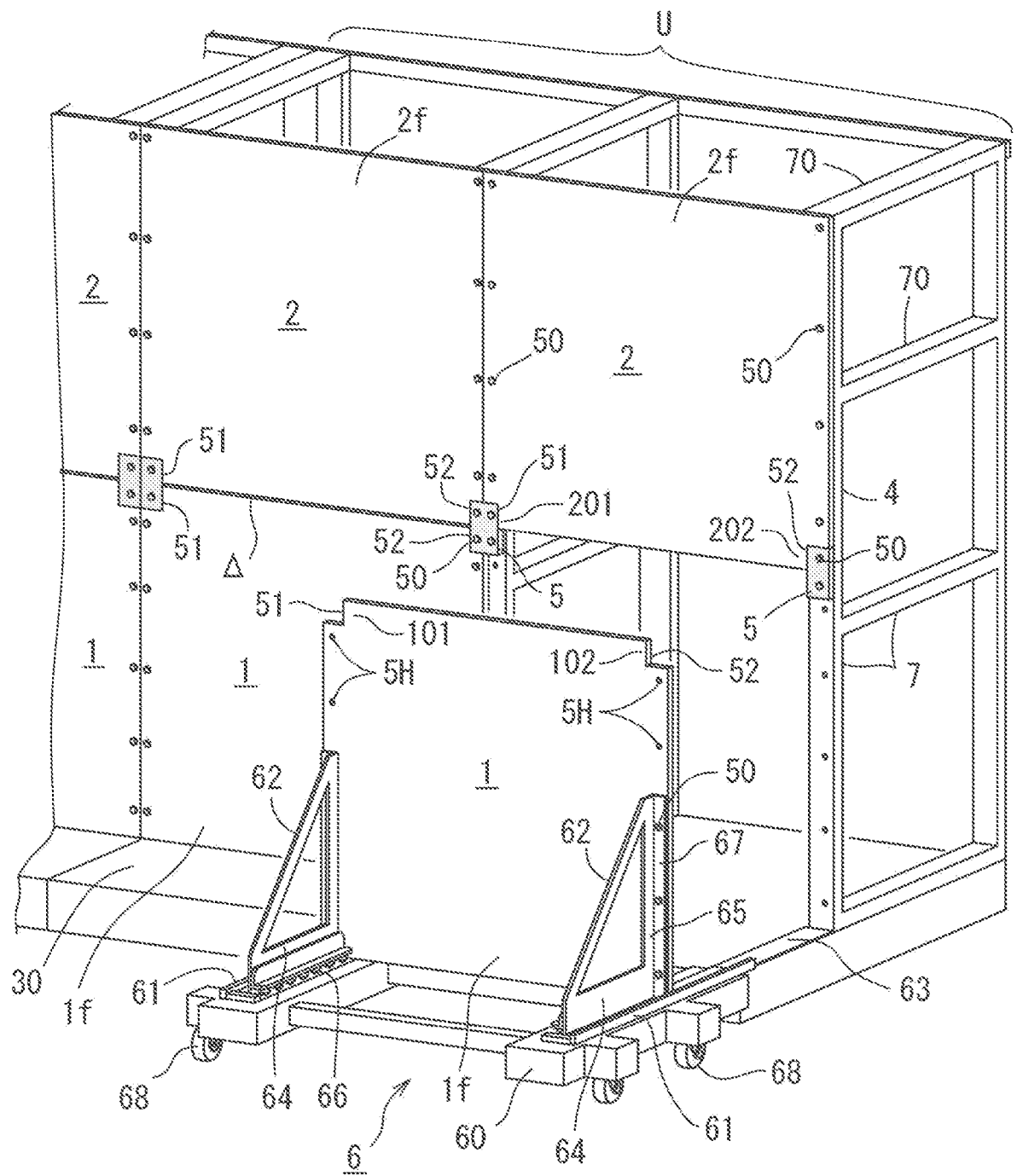
FIG. 4 is a schematic perspective view illustrating the panel attachment structure in the state where the lower panel is removed from pillars.

In this example, as shown in FIG. 10B and FIG. 4, the first notch 51 is formed in the first corner 201 of the upper panel 2 and the first corner 101 of the lower panel 1. At the same time, the second notch 52 is formed in the second corner 202 of the upper panel 2 and the second corner 102 of the lower panel 1.

As shown in another example of FIG. 10C, only the first and second corners 201 and 202 of the upper panel 2 may include notches whereas the first and second corners 101 and 102 of the lower panel 1 may not include notches. Alternatively, as shown in the example of FIG. 10D, only the first and second corners 101 and 102 of the lower panel 1 may include notches whereas the first and second corners 201 and 202 of the upper panel 2 may not include notches.

Each frame unit U may include a front face door, a back face door, and a ceiling board.

As shown in FIG. 6, the first and second processing sections 11 and 21 are attached to the front face 1f of the lower panel 1 and the front face 2f of the upper panel 2 as shown by the two-dot chain line, respectively. On the other hand, the first and second driving sections 12 and 22 are attached to the back face 1b of the lower panel 1 and the back face 2b of the upper panel 2, respectively, as shown by the two-dot chain line. Although not shown, each of the panels 1 and 2 includes a penetration hole receiving a shaft connecting the processing sections to the respective driving sections.

Each of the processing sections 11 and 21 may be a die cut roller, an anvil roll, or a conveyor for example. On the other hand, each of the driving sections may be a servo motor to drive a roll to rotate, or a gear to transmit the driving force of a main motor of the entire equipment to the processing section.

This manufacturing equipment may be a manufacturing equipment for a wearable article such as a disposable diaper or disposable shorts, or sanitary products, for example.

In FIG. 6, the lower panel 1, the first processing section 11, and the first driving section 12 constitute the first unit 10. On the other hand, the upper panel 2, the second processing section 21, and the second driving section 22 constitute the second unit 20. To replace a device in this manufacturing equipment, the first unit 10 or the second unit 20 is replaced as a whole, for example.

Figure 2:
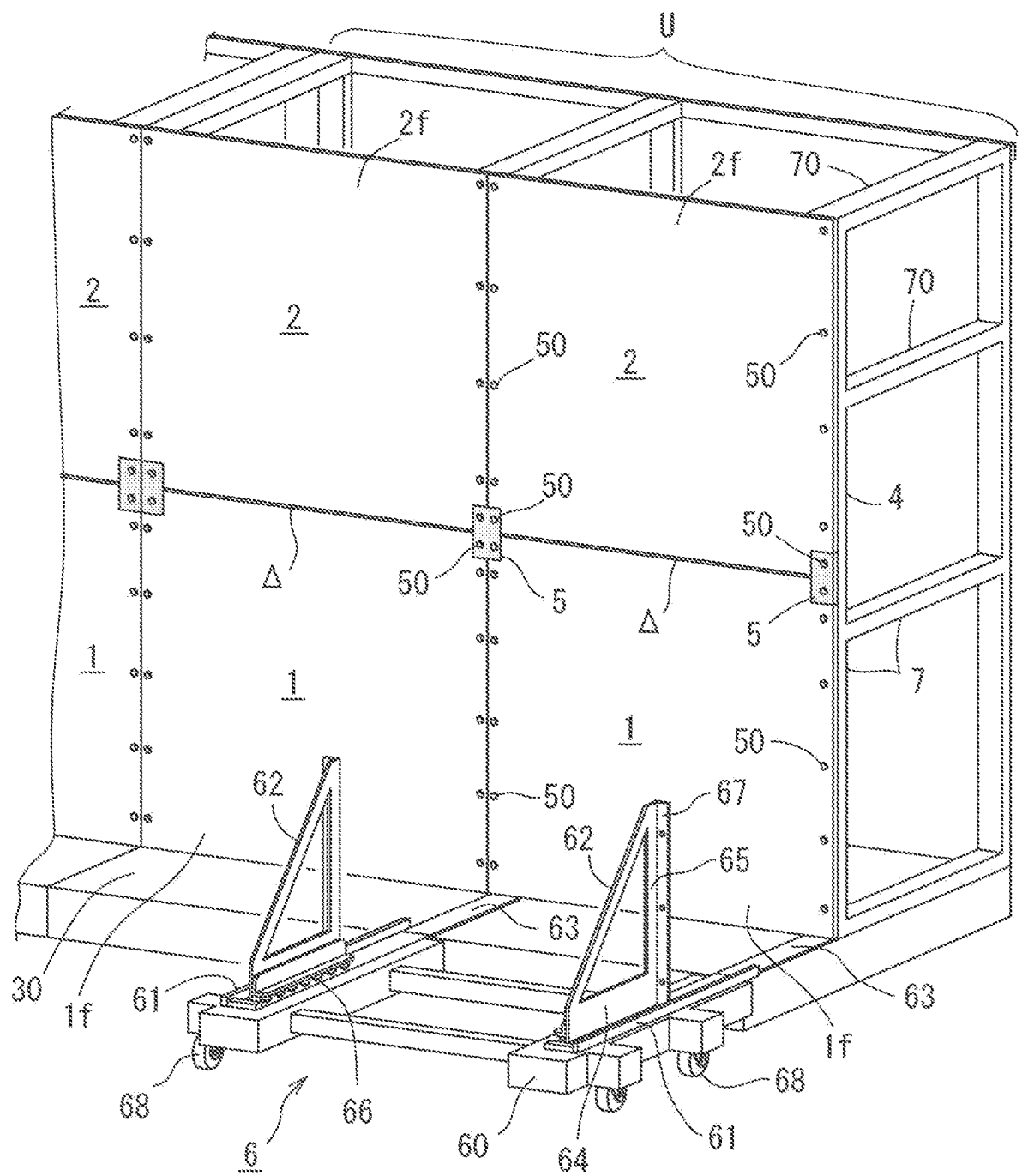
FIG. 2 is a schematic perspective view illustrating the panel attachment structure together with a replacement apparatus.

Next, the following section will describe the replacement unit 6 of the first unit 10 of FIG. 2.

In FIG. 2, the replacement unit 6 includes the carriage 60, a pair of guides 61, and a pair of sliders 62.

The carriage 60 is movable relative to the base 3 and transfers the first unit 10 via the base 3 as a platform. Note that the carriage 60 may have four casters 68, for example.

In the state where the carriage 60 is close to the base 3 functioning as a platform, the pair of guides 61 horizontally extends towards the lower panel 1, and protrudes from the carriage 60 as shown in FIG. 6. The pair of guides 61 has a height set along the upper face 30 of the base 3. Note that the guide 61 and the upper face 30 of the base 3 may have thereon a thin sliding plate 63.

Figure 3:
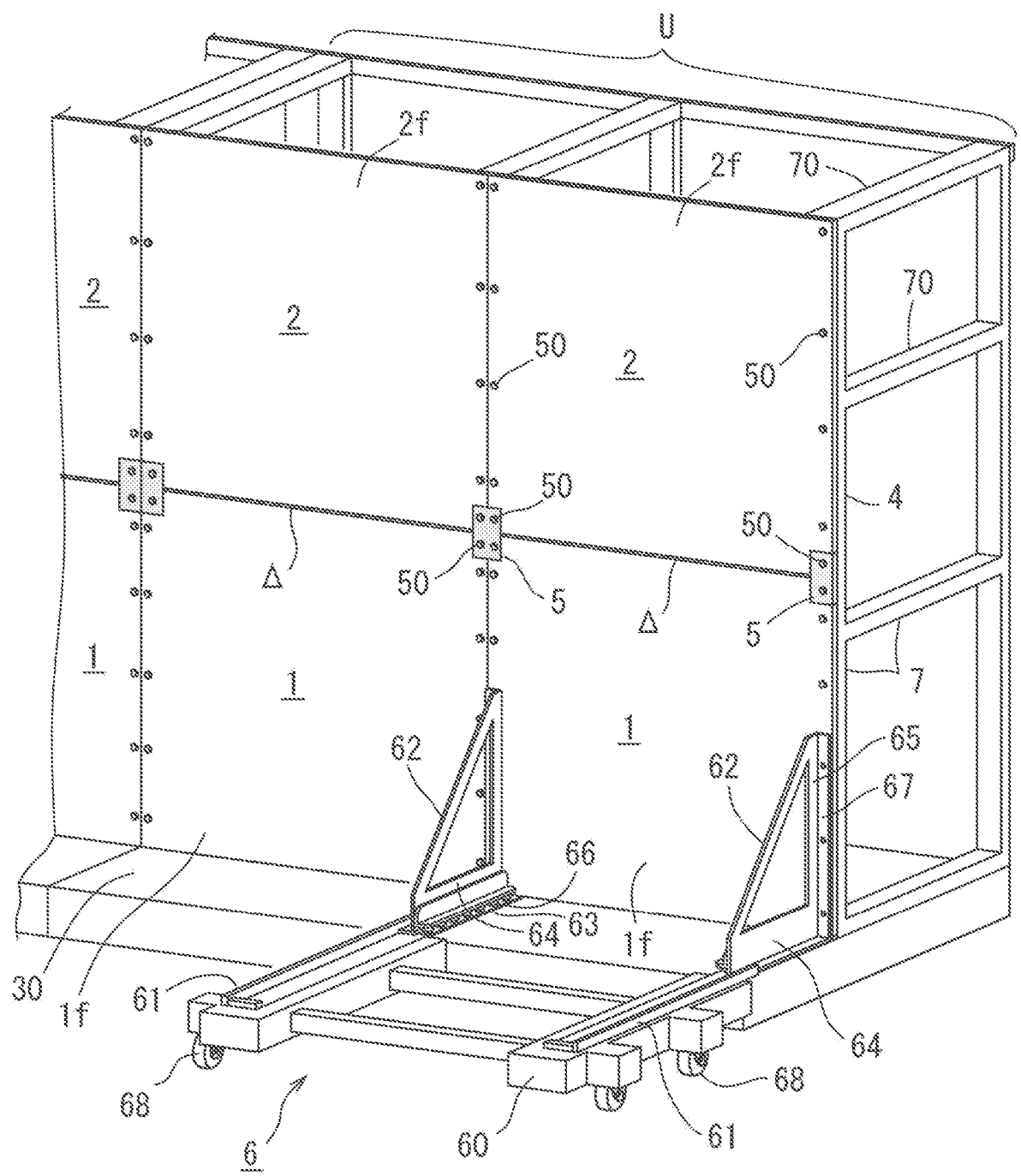
FIG. 3 is a schematic perspective view illustrating the panel attachment structure in the state where a slider is attached to a lower panel.

As shown in FIG. 2 to FIG. 4, the pair of sliders 62 can be slidably moved on the carriage 60 and the base 3 along the pair of guides 61. The sliders 62 are coupled with the lower panel 1 and are transferred together with the lower panel 1 from the surface of the base 3 onto the carriage 60. The slider 62 has a right angled triangle-like shape and has a frame-like shape.

In FIG. 4, the slider 62 includes a horizontal section 64 and a perpendicular section 65. A plurality of rollers 66 is attached to the horizontal section 64 in a rotatable manner so that the horizontal section 64 can slidably move on the base 3 and the carriage 60. On the other hand, the perpendicular section 65 is integrated with a flange 67 to which the lower panel 1 is tightened.

Note that an adjuster (not shown) may be provided that adjusts the height of the slider 62 in the up-and-down direction.

Next, the following section will describe a method of replacing only the first unit 10 while the second unit 20 is attached to the frame-like frame 7.

Hereinafter, this example will be described with regard to the replacement method using the replacement unit 6.

First, the substitute first unit 10A shown in gray in FIG. 8A to FIG. 8D is prepared prior to the following respective steps as a substitute unit for the first unit 10 shown in FIG. 7A to FIG. 7D.

The substitute first unit 10A is configured so that: the substitute lower panel 1A as a substitute for the lower panel 1 is attached to:
i) the substitute first driving section 12A as a substitute for the first driving section 12; and
ii) the substitute first processing section 11A as a substitute for the first processing section 11.

Here, the substitute lower panel 1A of FIG. 8A has a structure that can be attached to the frame-like frame 7 at least at the same position (portion) as where the lower panel of FIG. 1 has been fixed before replacement. For example, the substitute lower panel 1A (FIG. 8A) has at least a plurality of insertion holes 5H receiving the bolts 50 like the lower panel 1 of FIG. 4, and, as necessary, has a notch 51 corresponding to the support section 5.

The substitute lower panel 1A of FIG. 8A has a penetration hole so as to connect the substitute first processing section 11A to the substitute first driving section 12A.

The substitute first processing section 11A may be intended to process an article that has a different size from an article processed by the first processing section 11, or may have a different structure, or may have a similar structure having the same size. In other words, the substitute first processing section 11A may be any one so long as the substitute first processing section 11A can be replaced with the first processing section 11 as a part of the manufacturing equipment.

The substitute first driving section 12A may be intended to process an article that has a different size from an article processed by the first driving section 12, or may have a differed structure, or may have a similar structure having the same size. In other words, the substitute first driving section 12A may be any one so long as the first driving section 12A can be replaced with the first driving section 12 as a part of the manufacturing equipment.

The following respective steps are performed while the upper panel 2 provided directly above the lower panel 1 is fixed to the pair of pillars 4.

After the preparation of the substitute first unit 10A, as shown in FIG. 7A to FIG. 7D, the existing first unit 10 attached to the frame-like frame 7 is removed from the frame-like frame 7.

Figure 7A:
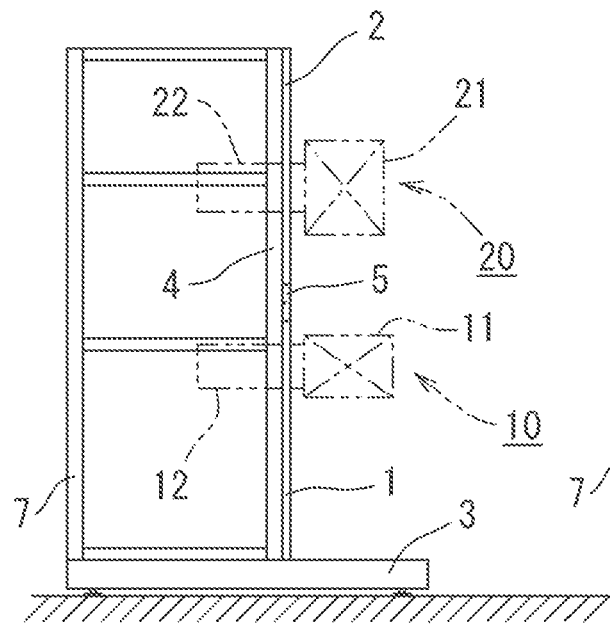
Figure 7B:
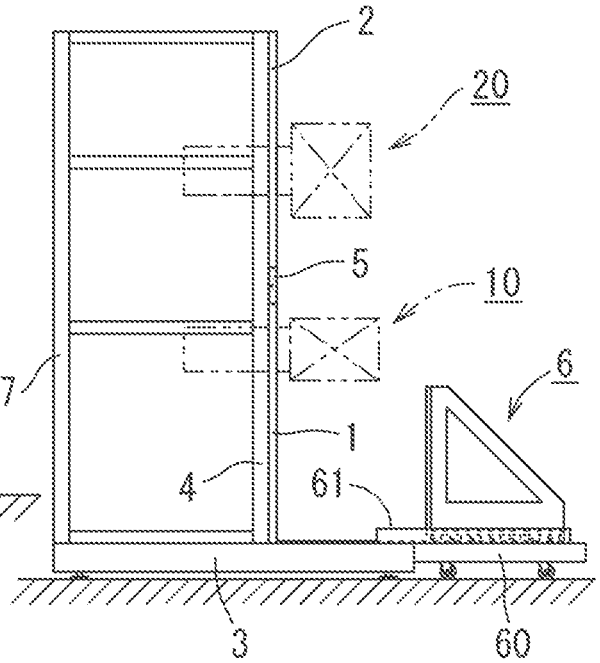

To perform this removal, first, as shown in FIG. 7B and FIG. 2, an approaching step is performed to move the carriage 60 close to the base 3 functioning as the platform. In this step, the pair of guides 61 on the carriage 60 is set to bridge over the carriage 60 and the base 3. Note that the base 3 of FIG. 6 may have thereon the sliding plate 63.

Figure 7C:
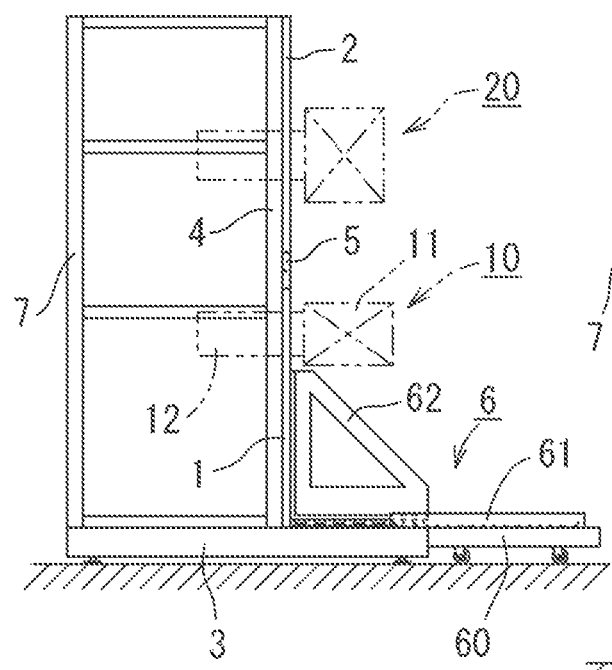

After the approaching step of FIG. 2, some bolts 50 of the lower panel 1 are removed, and the sliders 62 on the respective guides 61 are slid from the surface of the carriage 60 onto the base 3. Thereafter, as shown in FIG. 7C and FIG. 3, the coupling step is performed to couple the pair of sliders 62 with the lower panel 1 by bolts. This consequently allows the lower panel 1 and the pair of sliders 62 to have an integrated structure and prevents the first unit 10 from falling. Note that FIG. 3 shows a state before passing the bolts through the sliders 62.

Thereafter, the remaining bolts 50 by which the lower panel 1 of FIG. 3 is tightened to the pillar 4 are removed. Specifically, after the coupling step, a step is performed to remove the lower panel 1 from the pillar 4 to remove the first unit 10 from the pair of pillars 4.

Figure 7D:
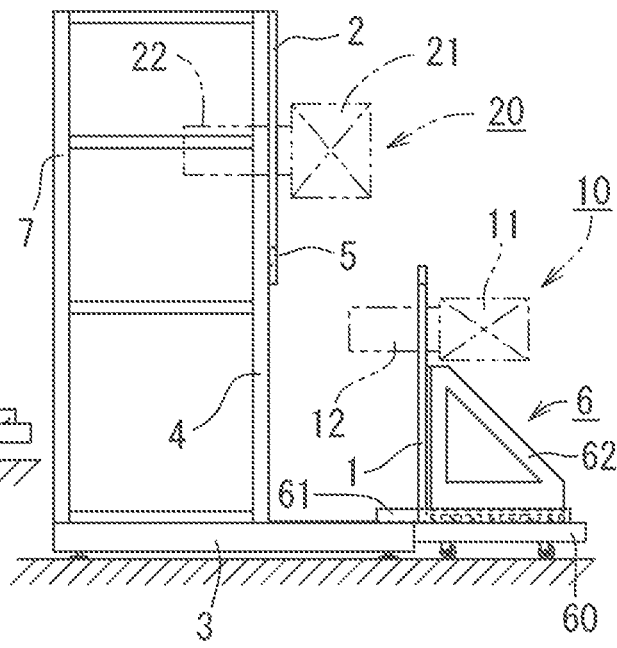

Thereafter, as shown in FIG. 7D and FIG. 4, a step is performed to transfer the first unit 10 together with the slider 62 onto the carriage 60 along the guide 61. During this, the first unit 10 is held by the pair of sliders 62 and thus is prevented from falling.

In this manner, the existing first unit 10 shown in FIG. 7A to FIG. 7D is removed from the frame-like frame 7.

Thereafter, as shown in FIG. 8A to FIG. 8D, a replacing step is performed, in an opposite order of the order of the above respective steps, to attach the first unit 10A, as a substitute for the first unit 10 removed from the pillar 4, to the pair of pillars 4 for the replacement.

Specifically, as shown in FIG. 8A, the pair of sliders 62 is coupled with the first unit 10A as a substitute via the substitute lower panel 1. After this coupling, the carriage 60 is moved close to the base 3 as a platform so that the guide 61 of the carriage 60 bridges over the carriage 60 and the base 3.

After the approaching step, as shown in FIG. 8A and FIG. 8B, a step is performed to transfer the substitute first unit 10A together with the slider 62 from the carriage 60 onto the base 3 along the guide 61. Note that the approaching step and the transfer step may be performed while the sliding plate 63 is provided on the base 3.

After the transfer, the substitute first unit 10A of FIG. 8B is fixed to the pillar 4 by some bolts 50 (FIG. 3) whereas the bolts 50 (FIG. 4) by which the substitute first unit 10A and the slider 62 are coupled are removed.

Thereafter, as shown in FIG. 8C, the slider 62 is slid from the surface of the base 3 onto the carriage 60 and is retracted. Further, as shown in FIG. 8D, the carriage 60 is moved to a predetermined storage space.

In this manner, as a substitute for the first unit 10 of FIG. 7D, the substitute first unit 10A of FIG. 8D is attached to the frame-like frame 7.

Incidentally, in the embodiment, the second panel 2 was attached with the second processing section 21 and the second driving section 22. However, the second panel 2 may be attached with a free roller, a shaft, or another not-driven device. When a not-driven device is provided on the front face 2f of the second panel 2, the second panel 2 may not include a penetration hole.

As described above, preferred examples have been described with reference to the drawings. However, various changes and modifications may be clear for those skilled in the art in view of this specification, within an obvious scope.

For example, the spacer 5 may be welded to the pillar 4 or may be fixed to the pillar 4 by one bolt.

A notch corresponding to the spacer 5 may be provided only in one panel of the upper and lower panels.

Thus, such changes and modifications will be interpreted as being within the scope of the present invention determined based on the claims.

INDUSTRIAL APPLICABILITY

The present invention can be applied to wearable articles such as a disposable diaper or shorts, as well as absorbing articles such as sanitary products.

Description of Reference Numerals

1: Lower panel 101: First corner 102: Second corner
2: Upper panel 201: First corner 202: Second corner
1f,2f: Front face 1b,2b: Back face
10: First unit 11: First processing section 12: First driving section
20: Second unit 21: Second processing section 22: Second driving section
3: Base 30: Upper face 31: Leg section
4: Pillar 40: Concave section
5: Support section (spacer) 50: Bolt 51: First notch 52: Second notch 5H: Insertion hole
6: Replacement unit 60: Carriage 61: Guide 62: Slider 63: Sliding plate
64: Horizontal section 65: Perpendicular section 66: Roller 67: Flange 68: Caster
7: Frame-like frame 70: Beam
Δ: Space
U: Frame unit

The invention claimed is:

1. A replacement unit for replacing a first processing section or a first driving section, the first processing section and the first driving section constituting a part of a wearable article manufacturing equipment,
the manufacturing equipment including:
one set of a lower panel and an upper panel that are arranged along a vertical plane and that are provided while being separated in an up-and-down direction;
the first processing section attached to a front face of the lower panel;
the first driving section attached to a back face of the lower panel;
a base that is provided under the lower panel and that is arranged along a horizontal plane; and
a pair of pillars raised from the base,
wherein the lower panel is removably fixed to the pair of pillars in a state of being laid between lower parts of the pair of pillars,
the upper panel is removably fixed to the pair of pillars in a state of being laid between upper parts of the pair of pillars, and
support sections are provided on respective pillars of the pair of pillars, the support sections being arranged between the upper panel and the lower panel, and supporting the load of the upper panel,
the replacement unit comprises:
a carriage movable relative to the base;
a pair of guides that extends toward the lower panel in a horizontal direction in a state where the carriage is close to the base functioning as a platform; and
a slider that is able to slide over the carriage and the base along the pair of guides, the slider being able to be coupled with the lower panel, and the slider being movable from the base to the carriage after coupled with the lower panel.

2. A method of replacing a first unit by using the replacement unit according to claim 1, the first unit including the lower panel, the first processing section, and the first driving section, the method comprising:
a step of moving the carriage close to the base that functions as the platform;
a coupling step of coupling the slider with the lower panel;
a step of removing, subsequent to the coupling step, the lower panel from the pair of pillars in order to remove the first unit from the pair of pillars;
a step of transferring the first unit and the slider onto the carriage along the guide; and
a step of replacing the first unit with a substitute first unit by attaching the substitute first unit to the pair of pillars, the substitute first unit being as a substitute for the first unit that has been removed from the pair of pillars, wherein
the moving step, the coupling step, the removing step, the transferring step, and the replacing step are performed in a state where the upper panel is fixed to the pair of pillars.

3. The method of replacing the first unit according to claim 2, wherein:
the support sections are spacers each fixed to an intermediate part of each of the pair of pillars, the intermediate part being positioned between each of the upper parts and each of the lower parts,
the step of replacing is performed in a state where the spacers provide a space between the lower panel and the upper panel by contacting with respective parts of a lower end of the upper panel.

* * * * *